United States Patent [19]

Chu et al.

[11] Patent Number: 5,252,747
[45] Date of Patent: Oct. 12, 1993

[54] CHIRAL QUINOLONE INTERMEDIATES

[75] Inventors: Daniel T. Chu, Downers Grove; Qun Li, Gurnee, both of Ill.

[73] Assignee: Abbott Laboratories, Abbott Park, Ill.

[21] Appl. No.: 943,946

[22] Filed: Sep. 11, 1992

[51] Int. Cl.$^5$ .............. C07C 101/04; C07C 121/43; C07D 207/24; C07D 207/14; C07D 207/12
[52] U.S. Cl. .................. 548/541; 548/557; 560/38; 562/443; 558/452
[58] Field of Search .............. 548/541, 557; 560/38; 562/443; 558/452

[56] References Cited

U.S. PATENT DOCUMENTS

| | | | |
|---|---|---|---|
| 4,210,660 | 7/1980 | Takeshima et al. | 424/274 |
| 5,144,072 | 9/1992 | Seido et al. | 548/541 |

FOREIGN PATENT DOCUMENTS

| | | | |
|---|---|---|---|
| 0197264 | 12/1982 | Japan | 548/541 |
| 2-246551 | 10/1987 | Japan | 548/541 |
| 0112962 | 5/1991 | Japan | 548/541 |

OTHER PUBLICATIONS

Rosen et al., *J. Med. Chem.* 31(8):1598–1611 (1988).

Primary Examiner—David B. Springer
Attorney, Agent, or Firm—Andreas M. Danckers

[57] ABSTRACT

Chiral compounds having the formulae

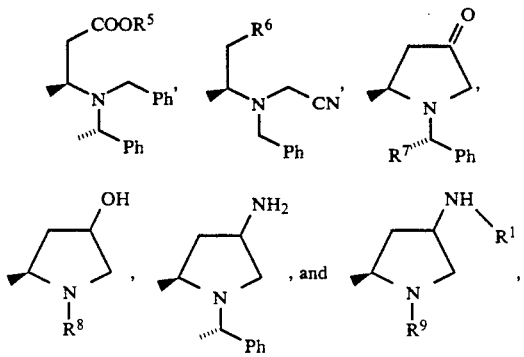

useful in the synthesis of quinolone intermediates.

11 Claims, No Drawings

CHIRAL QUINOLONE INTERMEDIATES

TECHNICAL FIELD

The present invention relates to chiral synthetic intermediates and the means of their preparation. More particularly, the invention relates to chiral amino-protected 4-amino-2-methylpyrrolidinines as well as compounds and procedures useful in the preparation thereof.

BACKGROUND OF THE INVENTION

The compounds of formula II, below, are useful intermediates in the preparation of certain quinolone antibacterial agents. For example, BOC -or acetyl- protected (2S,4S)-4-amino-2-methylpyrrolidine (II, in which $R^2$ is -BOC or acetyl) are intermediates in the synthesis of 7-((2S,4S)-4-amino-2-methyl-1-pyrrolidinyl)-1-(2,4-difluorophenyl)-1,4-dihydro-6-fluoro-4-oxo-quinolone-3-carboxylic acid, the preparation of which is described in U.S. Pat. No. 4,962,112.

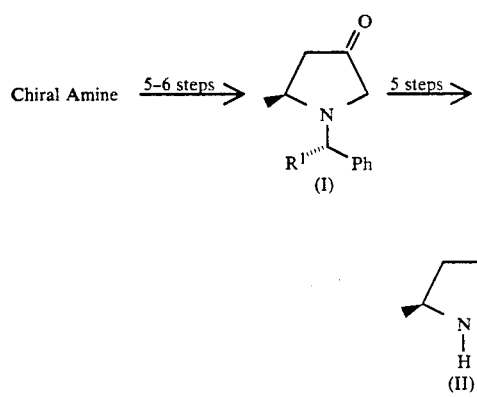

Reported syntheses of compounds II are limited in their ability to provide stereochemically pure products with a minimum of reaction steps, and in the availability of the necessary starting materials. Thus there is a continuing need to develop more effective syntheses of II. The compounds and process of the present invention enable the production of compound II from starting materials which are readily available and/or with yields which were previously unattainable.

SUMMARY OF THE INVENTION

The compounds of the present invention are chiral intermediates having the formula

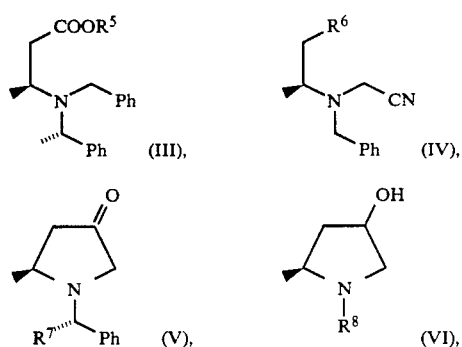

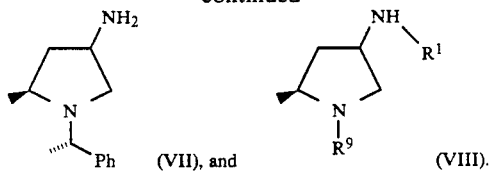

In the above formulae,
Ph is phenyl;
$R^1$ is selected from the group consisting of t-BOC and acetyl;
$R^5$ is hydrogen or loweralkyl;
$R^6$ is selected from the group consisting of hydroxy, halo and cyano;
$R^7$ is selected from the group consisting of hydrogen and methyl;
$R^8$ is selected from the group consisting of —$CH_2C_6H_5$ and —$CH(CH_3)C_6H_5$; and
$R_9$ is selected from the group consisting of —$CH_2C_6H_5$ and —$CH(CH_3)C_6H_5$.

Preferred among the compounds of the invention are those of formulae VI and VIII wherein the chiral carbon atom at C-4 has either the R- or the S-configuration.

The process of the present invention comprises a means of preparing a trans-configuration amino-protected 4-amino-2-methylpyrrolidine compound having the formula

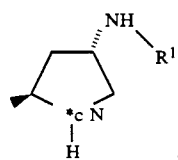

According to the process, a corresponding trans-configuration N-1-protected intermediate of the formula

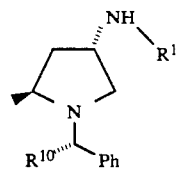

is selectively crystallized from a (4R)- and (4S)-configuration mixture of said intermediate, in which $R^1$ is t-BOC or acetyl, and $R^{10}$ is hydrogen or methyl.

DETAILED DESCRIPTION OF THE INVENTION

In the specification and claims hereof, the following terms have been accorded the meanings below:

The term "alkanoyl" refers to a radical of the formula —$C(O)R^{11}$ where $R^{11}$ an alkyl group as defined below, such as acetyl.

The term "alkoxy" refers to a radical of the formula —$OR^{12}$ where $R^{12}$ is an alkyl group as defined below, and includes, but is not limited to, methoxy, ethoxy and propoxy.

The term "alkyl" refers to a monovalent radical derived from a branched or straight chain aliphatic hydrocarbon of from 1 to 6 carbon atoms by the removal of one hydrogen atom. Examples include, but are not limited to, methyl, ethyl, propyl, isopropyl, n-butyl, t-butyl and neopentyl.

The term "alkylamino" refers an amino radical having one to three alkyl substituents, as defined above. Examples include methylamino, ethylamino and dimethylamino.

The term "aminoalkyl" refers to an alkyl radical, as defined above, substituted with an amino group; examples include aminoethyl and aminomethyl.

The term "alkylsulfonyl" refers to an alkyl radical as defined above bonded to a sulfonyl group, such as for example ethylsulfonyl or methylsulfonyl.

"BOC" or "t-BOC" refers to a t-butyloxycarbonyl protecting group.

The term "carboxy-protecting group" refers to the residue $R^{13}$ of a carboxylic acid ester group —COOR$^{13}$. Such carboxy-protecting groups are well known to those skilled in the art, having been extensively used in the protection of carboxyl groups in the penicillin and cephalosporin fields as described in U.S. Pat. Nos. 3,840,556 and 3,719,667, the disclosures of which are incorporated by reference. In general, such carboxy-protecting groups can be relatively easily cleaved to yield the free carboxy group. Representative protecting groups include $C_1$-$C_8$ alkyl (such as methyl, ethyl and tert-butyl), substituted alkyl (such as dimethylaminoethyl), and benzyl and substituted benzyl such as alkoxybenzyl and nitrobenzyl groups; also suitable are acyl groups such as pivaloyloxymethyl groups. See for example, T. H. Greene, "Protective Groups in Organic Synthesis", John Wiley and Sons, New York, (1981), incorporated herein by reference.

The term "halogen" or "halo" refers to a chloro, bromo, fluoro or iodo radical.

The term "halo-substituted alkyl" refers to an alkyl radical, as defined above, in which between one and three hydrogen atoms are replaced with the same or different halogen atoms. Examples of halo-substituted alkyls of from 1 to 6 carbon atoms include fluoromethyl, trifluoromethyl and fluoroethyl.

The term "loweralkyl" refers to an alkyl group as defined above containing one to six carbon atoms.

The term "phenyl" refers to optionally substituted benzene rings having up to three non-hydrogen substituents independently selected from halogen and alkyl.

The compounds of the present invention are intermediates in a process whereby a chiral amine is converted via several steps to a novel chiral intermediate pyrrolidinone compound of formula I, above, wherein $R^7$ may be hydrogen or lower alkyl such as methyl. This pyrrolidinone is subsequently converted to a N-protected 2S,4S-chiral compound of formula II, wherein $R^1$ is selected from the group consisting of alkanoyl such as acetyl.

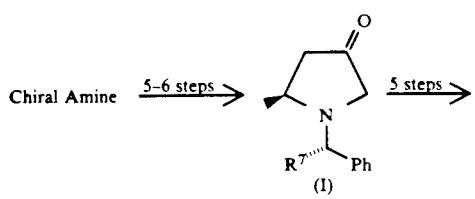

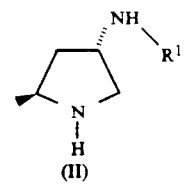

The preparation and utilization of the compounds of the present invention will be better understood in connection with the following reaction schemes. In Scheme 1, (S)-alpha-methylbenzylamine of formula 1 is converted into the benzyl-protected compound of formula 2 by reaction with benzaldehyde in an alcohol, such as methanol or ethanol, at a temperature of from 5° to 30° C. for 0.5 to 3 hours followed immediately by reduction of the intermediate with a borohydride reducing agent, for example sodium borohydride or sodium tricyanoborohydride, at from 10° to 35° C. for 2 hours in the same vessel.

The compound of formula 2 is then converted to its lithium salt by reaction with n-butyl lithium in THF at temperature of less than 0° C. Addition of an alkyl ester of trans-2-butenoic acid of formula 3, where $R^2$ is lower alkyl, to the above solution at a temperature of from −78° C. to 0° C. produces the (3S)-3-(protected-amino)butanoic ester of formula 4.

The benzyl groups are then removed from the compound of formula 4 by hydrogenolysis, for example with formic acid, ammonium formate or hydrogen in the presence of a catalyst such as Pd/C in a solvent such as methanol or ethanol, to give the (3S)-3-aminobutanoic acid ester of formula 5. The compound of formula 5 is re-protected and converted to the benzyl-protected compound of formula 6 by reaction with benzaldehyde and reduction as described above. The compound of formula 6 is then reacted with an alpha-haloacetic acid ethyl ester, such as ethyl chloracetate or ethyl bromoacetate, to produce the diester compound of formula 7. Ring closure to the compound of formula 8 (compound I, where $R^1$ is hydrogen) is accomplished by a 2-part reaction of the compound of formula 7 first with a base such as sodium ethoxide or potassium t-butoxide in a solvent such as toluene, ethanol or methanol under nitrogen at a temperature from 0° C. to room temperature for from 1 to 4 hours, followed by concentration and acidification of the intermediate with 6N hydrochloric acid at reflux for 3-6 hours or until evolution of carbon dioxide ceases. Reduction of the cyclic ketone compound of formula 8 to the alcohol compound of formula 9 may be accomplished with various reducing agents, as for example sodium borohydride, lithium aluminum hydride, L-, K- and LS-SELECTRIDE borohydride ketone-reducing reagents, diisobutylaluminum hydride, lithium tri-t-butoxyborohydride, or catalytic reduction with hydrogen over noble metal catalysts, in an appropriate solvent such as methanol, ethanol, THF, toluene or methylene chloride at a wide range of temperatures from −78° C. to room temperature for between 1 and 18 hours.

The ratio of cis to trans isomers of compound 9 formed may vary from about 1:1 to about 10:1 depending upon the specific conditions chosen, and it is preferable to chose conditions such that this ratio is greater than 6:1. The desired cis isomer may separated from the trans isomer by standard chromatographic methods, but selective crystallization is to be preferred over chromatographic means. Here, it is surprisingly found that selective crystallization is considerably favored by the amino-protection of an N-1-substituted 4-amino-2-methylpyrrolidine with either an acetyl or a BOC group.

The compound of formula 10 is converted to the free amino compound of formula 11 by reaction with hydrazine monohydrate in ethanol under reflux conditions for 1 to 5 hours, or by hydrolysis with inorganic acids or bases. The compound may be isolated as the HCl salt, and the free amine may be extracted from an aqueous

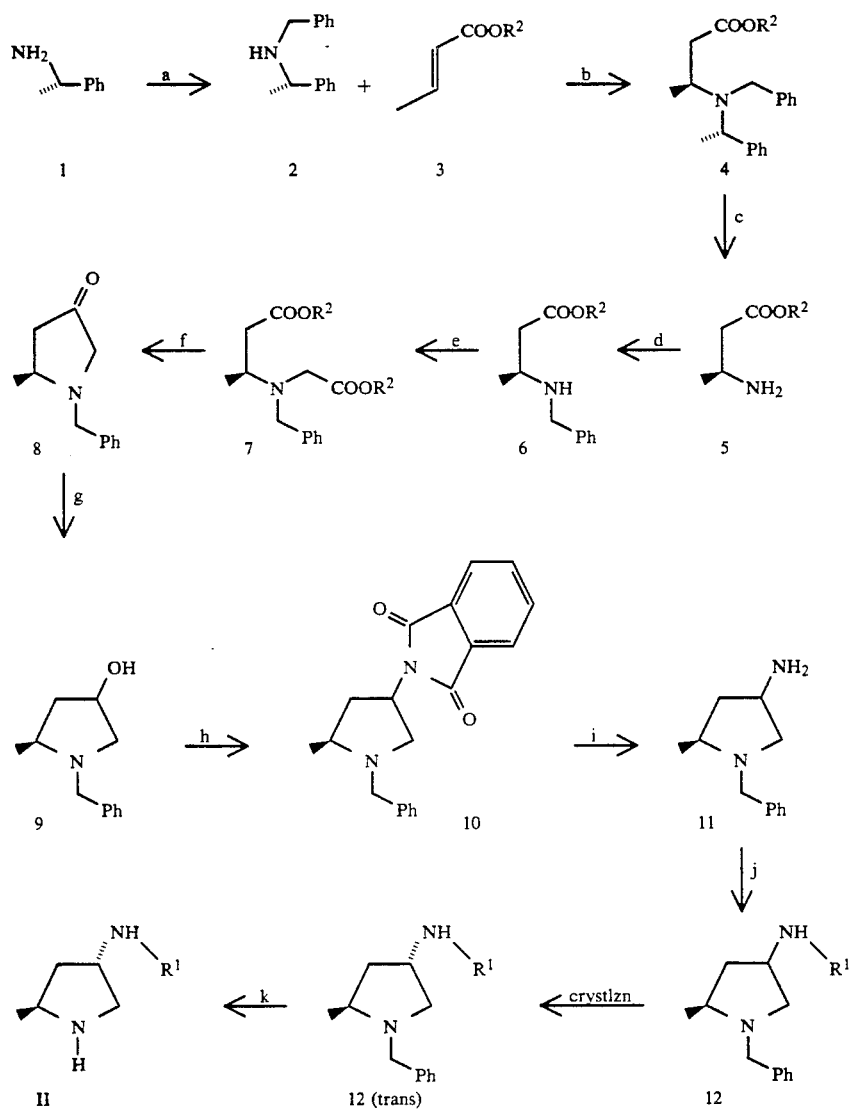

Scheme 1 solution at pH 14. The free amino compound of formula 11 is converted to the acetyl-protected compound of formula 12 (where $R^1$ is acetyl) by stirring with triethylamine and acetic anhydride for 12 to 18 hours at room temperature. (The reactions proceed by converting the cis isomer of 9 to the trans isomer of 12 and the trans isomer of 9 to the cis isomer of 12. In the event that it is desirable to separate the cis and trans isomers of 12 at this point, this may be done by selective recrystallization. For example, recrystallization from 1:4 ethyl acetate:hexane results in the pure crystalline trans isomer of compound 12. Should the cis isomer be desired, it may be isolated by chromatography from the mother liquor.)

Alternatively, the compound of formula 11 is converted into the BOC-protected compound of formula 12

It is generally desirable to postpone the separation of the cis and trans isomers, and to proceed through steps g, h, i and j of Scheme 1 with the mixture of diastereomers, separating the cis and trans compounds of formula 12 by crystallization after selective enrichment of the major trans isomer and resulting in a compound of formula 12 that is essentially isomerically pure. Alternatively, the mixture of isomers of compound 9 may be taken to the next step, and the diastereomers of compound 10 separated after that reaction.

The alcohol compound of formula 9 may be converted to the compound of formula 10 by reaction with phthalimide in the presence of diethyl azodicarboxylate (DEAD) or diisopropyl azodicarboxylate (DIAD) and triphenylphosphine in anhydrous THF under nitrogen and anhydrous conditions at 20° C. for 0.5 hours.

(in which R¹ is BOC) by reaction with di-t-butyl carbonate in methanol. At this point the cis and trans compounds of formula 12 by are purified by crystallization to selectively yield the desired trans isomer in an isomerically pure form. The protected compounds of formula 12 are converted to the compounds of formula 2 by removal of the benzyl protecting group as described above.

If it is desired to produce the cis (2S,4R) isomers of compounds of formulas 11, 12 and II, this may be accomplished by following the reaction sequence i-j-k of Scheme 1, isolating and proceeding with the cis compound of formula 9, and omitting the selective crystallization step before step k.

In an alternate process starting with the racemic compound 8 (prepared according to Prost et al., Helv. Chim. Acta 52, 1134 (1969)) instead of the chiral compound 8, a mixture of isomers may be carried through steps g, h, i and j as described for Scheme 1, followed by crystallization to remove the minor cis isomers. The remaining enantiomeric pair is resolved to isolate the desired 2S,4S compound 12 by the use of (+)-tartaric acid or its derivatives or another optically active acid (for additional information see P. Newman, *Optical Resolution Procedures for Chemical Compounds: Vol 1. Amines and Related Compounds*, Optical Resolution Information Center, New York, 1978). Compound 11 may also be resolved by this method. This isomerically pure compound is then N-protected as in step j and debenzylated as in step k of Scheme 1 to produce the desired chiral compound II. This process has a maximum yield of 50%, by virtue of starting with a racemic compound.

In an alternate process of preparing the compound of formula II, the compound of formula 4 may be converted by the Scheme 1A below into the compound of formula 13 by selective hydrolysis using noble metal catalysts, such as for example Pd/C, and hydrogen chloride in a solvent such as methanol, ethanol or methoxymethanol. The compound of formula 13 may then be converted into the compound of formula 14 by a procedure similar to that described for Scheme 1 above. This compound is then cyclized to the compound of formula 15 by the method also described above. The compound of formula 15, which is analogous to the compound of formula 8 of Scheme 1, may be converted to the compound of formula II by steps similar to those described for procedures g, h, i, j and k in Scheme 1 above.

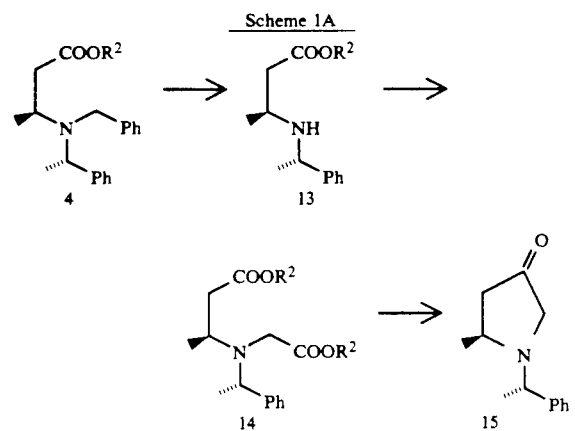

An alternative process for preparing the compound of formula 8 is shown in Scheme 2. In accordance with Scheme 2, (R)-2-aminopropanol of formula 16 is converted into the benzyl-protected compound of formula 17 by the reaction described in Scheme 1 above. The benzyl-protected compound of formula 17 is converted into the cyanoalcohol compound of formula 18 by reaction with formaldehyde in sodium bisulfite solution at a temperature from 20° to 60° C. for from 2 to 20 hours, followed by immediate reaction in the same reaction vessel with sodium cyanide at from 0°-20° C. with stirring for from 1 to 20 hours.

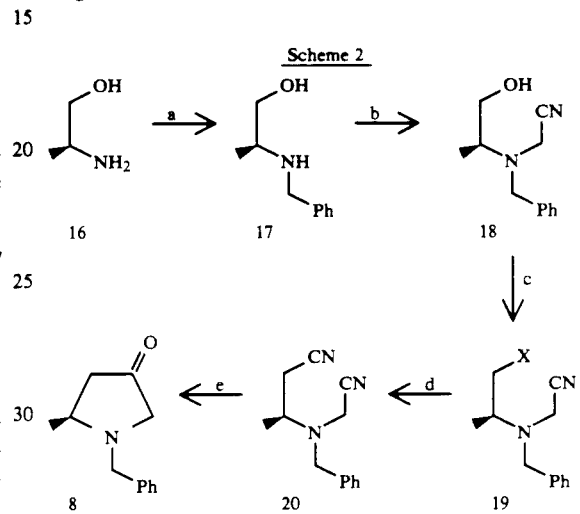

The cyanoalcohol compound of formula 18 is converted to the halocyano compound of formula 19 by reaction with triphenylphosphine and a halogenating agent, such as carbon tetrachloride, carbon tetrabromide or methylsulfonyl chloride in chloroform or methylene chloride under nitrogen and anhydrous conditions. The reaction may be run at temperatures from 0° C. to room temperature for periods of from 8 to 24 hours. The halocyano compound of formula 19 is converted to the dicyano compound of formula 20 by reaction with sodium or potassium cyanide in a polar solvent such as ethanol, DMF or DMSO at a temperature from 50°-80° C. for from 8 to 24 hours under a nitrogen atmosphere. Ring closure to the compound of formula 8 is accomplished by reaction of the dicyano compound of formula 20 with a base such as sodium ethoxide or potassium t-butoxide in a solvent such as toluene, ethanol or methanol under nitrogen at a temperature from 0° C. to room temperature for from 1 to 4 hours. After concentration, the intermediate is acidified with concentrated hydrochloric acid and stirred for 24-72 hours at room temperature, then heated at 60° C. for 3 hours and then at 70°-80° C. for 5 hours, or until evolution of carbon dioxide ceases. The compound of formula 8 (I, in which R¹ is H) is then carried forward by the reactions described for Scheme 1.

The methods described in Schemes 1 and 2 may be applied to the synthesis of substituted pyrrolidines such as (2S,4S)-4-amino-alkylpyrrolidines.

Scheme 3

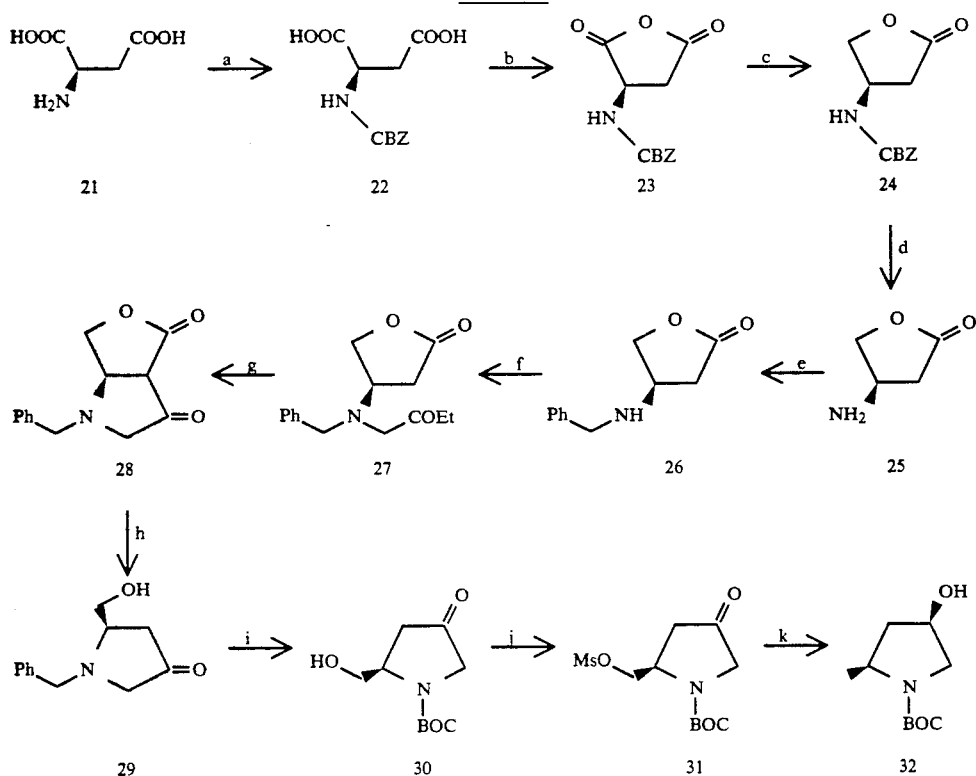

An alternative process for preparing chiral compounds of formula 9 is given in Scheme 3. In accordance with Scheme 3, D-aspartic acid of formula 21 is protected at the amino group by reaction with benzyloxycarbonyl chloride, for example, to produce the compound of formula 22. The protected amino diacid compound of formula 22 is then reacted with acetic anhydride in order to convert it into the anhydride compound of formula 23. The anhydride of formula 23 is reacted with sodium borohydride in methoxymethanol in order to produce the cyclic lactone of formula 24. The CBZ protecting group is removed from the compound of formula 24 by hydrogenolysis, with for example hydrogen or formic acid in the presence of a catalyst, or by hydrolysis with, for example, hydrobromic acid in acetic acid to produce the compound of formula 25. (The procedures for converting compound 21 into compound 25 are given in JACS, 110:8557 (1988) and Indian J. Chem Sect B, 278:1524 (1988), incorporated herein by reference.). This compound is reprotected with the benzyl group by reaction with benzaldehyde in an alcohol, such as methanol or ethanol, at a temperature of from 5° to 30° C., for 1 hour followed immediately by reduction of the intermediate with a borohydride reducing agent, for example sodium borohydride or sodium tricyanoborohydride, at from 10°–35° C. for 2 hours in the same vessel. The compound of formula 26 is then reacted with an alpha-haloacetic acid ethyl ester, such as ethyl chloracetate or ethyl bromoacetate, to produce the ester compound of formula 27. The bicyclic compound of formula 28 is produced from the compound of formula 27 by reaction with a strong base, such as potassium t-butoxide, sodium ethoxide, sodium bis-(trimethylsilyl)amide or the like, in a polar solvent, such as methanol, ethanol, or the like. By reacting the bicyclic compound of formula 28 with a strong acid, for example hydrochloric acid, the lactone ring is opened and a decarboxylation takes place to produce a hydroxy ketone compound of formula 29. The compound of formula 29 is debenzylated and reprotected with the BOC group by procedures described above. The compound of formula 30 is converted to a sulfonate compound of formula 31 by reaction with triphenylphosphine and a halogenating agent, such as carbon tetrachloride, carbon tetrabromide or toluenesulfonyl chloride or methylsulfonyl chloride in chloroform or methylene chloride under nitrogen and anhydrous conditions. The reaction may be run at temperatures from 0° C. to room temperature for periods of from 8 to 24 hours. The leaving group may be removed from compounds of formula 30 to produce the compound of formula 32 by reaction with a reducing agent, for example lithium aluminum hydride or lithium triethylborohydride in a solvent such as THF or ether. The compound of formula 32 in turn may be converted to compounds of formula 1 by substituting the compound of formula 32 for the compound of formula 9 and following the subsequent reaction steps indicated by h, i, j, and k for Scheme 1 as described above.

In another alternative synthetic route, the cis compound of formula 9 may be debenzylated and reprotected with BOC, in a manner as described for the conversion of compound 29 to compound 30 in Scheme 3, in order to convert it directly into the compound of formula 32.

Scheme 4

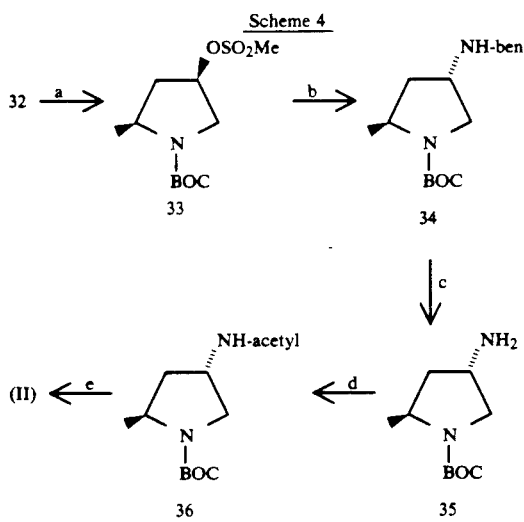

In accordance with Scheme 4 above, the compound of formula 32 is converted to a sulfonate compound of formula 33 by the reactions described for Scheme 3 above. The leaving group of the compounds of formula 33 are replaced with the substituted amine group to give compounds of formula 34 by reaction with benzylamine under nitrogen at a temperature of from 100° C. to 110° C. The benzyl group of compounds of formula 34 is removed by the procedure described for Scheme 1 above to give the compounds of formula 35. The acetyl group is added to compounds of formula 35 to produce compounds of formula 36 by the reaction described for Scheme 1 above. The final hydrolysis of compounds of formula 36 to compounds of formula II may be accomplished with a strong acid, such as hydrochloric acid or trifluoroacetic acid at room temperature The foregoing may be better understood by reference to the following examples, which are provided for illustration only and are not intended as a limitation upon the scope of the invention.

EXAMPLE 1

(2S, 4S)-4-Acetylamino-1-benzyl-2-methylpyrrolidine

Step 1a. (S)-2-Benzylamino-1-propanol (17)

Via a procedure similar to that in J. Heterocyclic Chem. 11:807 (1974), to 51.15 g (0.681 mol) of (S)-amino-1-propanol in 400 mL of methanol was added 72.30 g (0.681 mol) of benzaldehyde slowly with stirring at room temperature. This exothermic reaction was stirred for 1 hour. The reaction vessel was cooled to 20°-25° C. with a water bath, and 19.15 g (0.506 mol) of sodium borohydride was added over a period of 1 hour at a rate such that the internal temperature did not exceed 30° C. The reaction was then stirred at room temperature for 1 hour, and the solvent was removed under vacuum. The residue was slurried with 500 mL of water and extracted 3 times with methylene chloride. The extracts were combined, washed with water, and dried over magnesium sulfate. The solvent was removed and the product was dried to afford 110.07 g (97.8% yield) of the title product as a white solid, which was taken to the next reaction without further purification.

Step 1b. (2S)-Benzyl-(1-hydroxy-2-propyl)aminoacetonitrile (18)

To a stirred solution of 83.25 g (0.800 mol) of sodium bisulfite in 170 mL of water at room temperature was added 60.0 mL (0.800 mol) of 37% formaldehyde. This solution was warmed to 60° C., held at this temperature for 10 minutes, then cooled to 35° C. To this solution was added 110.07 g (0.666 mol) of (S)-2-benzylamino-1-propanol, from step 1a, and the reaction was stirred for 2.5 hours. To the reaction solution was added 40.00 g (0.816 mol) of sodium cyanide in 100 mL of water. The exothermic reaction was stirred vigorously for 1.5 hours at room temperature. The organic layer was separated, combined with ether extracts of the aqueous layer, washed twice with brine, dried over magnesium sulfate and concentrated to give 135.56 g (99% yield) of the title product as a pale yellow oil. MS M/Z: 205 (M+H). NMR (CDCl$_3$)δ: 1.21 (3H, d, J=7.5 Hz), 2.47 (1H, dd, J=8, J=3 Hz), 3.30 (1H, m), 3.45 (1H, d, J=10.5 Hz), 3.46 (1H, d, J=10.5 Hz), 3.54 (2H, m), 3.70 (1H, d, J=13.5 Hz), 3.90 (1H, d, J=13.5 Hz), 7.34 (5H, m).

Step 1c. (2S)-Benzyl-(1-chloro-2-propyl)aminoacetonitrile (19)

To a stirred solution of 132.23 g (0.647 mol) of (S)-2-(N-Benzyl-N-cyanomethylamino)-1-propanol, from step 1b, in 500 mL of methylene chloride and 94 mL of anhydrous carbon tetrachloride under nitrogen and anhydrous conditions and at room temperature was added 170 g (0.648 mol) of triphenylphosphine. The mixture was stirred at room temperature, but soon the exothermic reaction raised the temperature to reflux temperature. The reaction was stirred for 22 hours, another 8.5 g (0.032 mol) of triphenylphosphine was added, and the reaction was stirred another 2.5 hours. Methanol was added to destroy the excess triphenylphosphine, and the mixture concentrated to dryness. The solid was triturated with ether and hexane, which were filtered and concentrated. The oil was redissolved in ether, hexane added, filtered, concentrated and chromatographed over a short silica gel column, eluting with 1:4 ethyl acetate:hexane to afford after removal of the solvent 112.31 g (77.9% yield) of the title product as a colorless liquid. MS M/Z: 223, 225 (M+H). NMR (CDCl$_3$) d: 1.35 (3H, d, J=6 Hz), 3.21 (1H, sextet, J=6 Hz), 3.48 (2H, s), 3.52 (2H, s), 3.57 (1H, dd, J=6, J=12 Hz), 3.68 (1H, dd, J=5, J=12 Hz), 7.35 (5H, m).

This reaction produced as a by-product (R)-N-(2-chloro-1-propyl)-N-cyanomethylbenzylamine; this, however, was converted to the correct dicyano compound in the next step via a transient intermediate in the conversion which is the same for the two compounds. MS M/Z: 223, 225 (M+H). NMR (CDCl$_3$)δ: 1.53 (3H, d, J=6 Hz), 2.82 (1H, dd, J=6, J=13.5 Hz), 2.90 (1H, dd, J=7, J=13.5 Hz), 3.52 (2H, s), 3.75 (2H, m), 4.80 (1H, m), 7.36 (5H, m).

Step 1d. (3S)-(3)-Benzyl-(cyanomethyl)aminobutanonitrile (20)

To 112.31 g (0.504 mol) of (S)-N-(1-chloro-2-propyl)-N-cyanomethylbenzylamine or the the mixture of compounds from step 1c, in 500 mL of anhdrous DMSO under nitrogen atmosphere was added 37.10 g (0.757 mol) of sodium cyanide. The reaction was stirred at 60° C. for 21 hours, slurried with water and extracted with ether. The extract was washed with brine, dried over magnesium sulfate, concentrated, and the residue chromatographed on silica gel, eluting with ethyl acetate:hexane in 1:4, 1:2, and 1:1 ratios to give 81.47 g (75.5% yield) of the title compound. MS M/Z: 231, 233 (M+NH$_4$). NMR (CDCl$_3$) δ: 1.41 (3H, d, J=6.5 Hz), 2.57 (1H, dd, J=6.5, J=16.5 Hz), 2.66 (1H, dd, J=6.5, J=16.5 Hz), 3.34 (1H, sextet, J=6.5 Hz), 3.48 (2H, s), 3.81 (2H, s), 7.36 (5H, m).

Step 1e. (S)-N-Benzyl-5-methylpyrrolidin-3-one (8)

To a stirred solution of the dicyano compound from step 1d (81.47 g, 0.382 mol) in 500 mL of toluene at 0° C. under a nitrogen atmosphere was added 47.10 g (0.419 mol) of potassium t-butoxide. The reaction was stirred at 0° C. for 30 minutes and at room temperature for 1.6 hours, then the solvent was removed to leave a yellow residue. To this residue was added 500 mL of concentrated hydrochloric acid slowly with ice bath cooling. The mixture was stirred for 65 hours, then heated at 60° C. for 3 hours, and 80° C. for 5 hours (until evolution of carbon dioxide ceased). The solution was concentrated, the residue made basic by addition of 2N sodium hydroxide, the mixture extracted with ether, the combined extracts washed with brine and dried over magnesium sulfate and concentrated to give a dark oil. This material was chromatographed over silica gel, eluting with 1:4 ethyl acetate:hexane to afford 42.83 g (59.2% yield) of the title compound after removal of the solvent. MS M/Z: 190 (M+H). NMR (CDCl$_3$) δ: 1.35 (3H, d, J=6 Hz), 2.14 (1H, dd, J=10, J=18 Hz), 2.50 (1H, dd, J=6 Hz, J=18 Hz), 2.64 (1H, d, J=17 Hz), 2.98 (1H, m), 3.24 (1H, d, J=17 Hz), 3.28 (1H, d, J=13 Hz), 4.20 (1H, d, J=13 Hz), 7.31 (5H, m). IR (neat): 1755 cm$^{-1}$. [a]$_D$= +212.4° (c=1.90, CHCl$_3$, 22°).

Step 1F. (2S,4R)-N-Benzyl-2-methylpyrrolidin-4-ol (9)

To 20.00 g (0.106 mol) of (S)-N-benzyl-5-methylpyrrolidin-3-one, from step 1e, dissolved in 200 mL of methanol and stirred at −78° C. was added 4.80 g (0.127 mol) of sodium borohydride. The reaction was allowed to warm to room temperature and stirred for 16 hours. The solvent was removed, the residue was slurried with 2N sodium hydroxide and extracted with ether, and the combined extracts were washed with saturated brine and dried over magnesium sulfate. The solvent was removed and the residual liquid was chromatographed over silica gel, eluting with 100:10:0.5 methylene chloride:methanol:ammonium hydroxide to afford the mixture of cis and trans amino alcohol products. The trans (2S,4S) product (2.09 g, 10.3% yield) solidified at 5° C., and 17.72 g (87.6% yield) of the cis (2S,4R) title product was separated as a viscous oil. cis: MS M/Z: 192 (M+H). NMR (CDCl$_3$) δ:1.23 (d, 3H, J=6 Hz), 1.46 (m, 1H), 2.70 (br, 1H), 2.19 (dd, 1H, J=4.5, J=10 Hz), 2.40 (m, 2H), 2.84 (d,1H, J=10 Hz), 3.14 (d, 1H, J=13 Hz), 4.05 (d, 1H, J =13 Hz), 4.12 (m 1H), 7.31 (m, 5H). trans: MS M/Z: 192 (M+H). NMR (CDCl$_3$)δ:1.16 (d, 1H, J=6 Hz), 1.82 (m, 2H), 2.18 (dd, 1H, J=5, J=10 Hz), 2.82 (m, 1H), 3.26 (d, 1H, J=10 Hz), 3.29 (d, 1H, J=13 Hz), 4.02 (d, 1H, J=13 Hz), 4.36 (m, 1H), 7.31 (m, 5H).

Step 1 g. (2S,4S)-4-Acetylamino-1-benzyl-2-methylpyrrolidine (12)

To 2.95 g (15.44 mmol) of the cis amino alcohol from step 1f in 50 mL of anhydrous THF held at 20° C. under a nitrogen atmosphere and anhydrous conditions was added 4.05 g (15.44 mmol) of triphenylphosphine and 2.27 g (15.44 mmol) of phthalimide. To this solution was added dropwise over ten minutes 2.45 mL (15.56 mmol) of diethyl azodicarboxylate (DEAD). The reaction was stirred for 20 minutes and the solvent was removed. The residue was dissolved in 25 mL of ethanol and 0.75 mL (15.46 mmol) of hydrazine monohydrate was added. The mixture was heated at reflux under nitrogen for 3 hours. 5 mL of concentrated hydrochloric acid was added and the yellow precipitate was filtered off and washed with ethanol. The filtrate was concentrated to dryness, the residue dissolved in water and filtered. The filtrate was concentrated, the residue dissolved in 200 mL of water and extracted with ether to remove residual triphenylphosphine. The aqueous solution was adjusted to pH 14 with 20% sodium hydroxide solution, extracted with ether, the extracts washed with water and dried over magnesium sulfate, and the solvent was removed to leave a pale yellow oil. This amino compound was dissolved in 30 mL of methylene chloride, and 4.0 mL of triethylamine and 3.0 mL of acetic anhydride was added. The mixture was stirred at room temperature for 16 hours, diluted, washed with water, dried over magnesium sulfate and concentrated to give a pale yellow solid. This material was chromatographed on silica gel, eluting with 100:5:0.5 methylene chloride:methanol:ammonium hydroxide to afford after removal of the solvent 3.01 g (83.9% yield) of the title product as a white solid. Alternately, the product can be purified by recrystallization from 1:3 ethyl acetate:hexane. MS M/Z: 233 (M+H). NMR (CDCl$_3$) δ: 1.16 (d, 3H, J=6 Hz), 1.74 (m, 1H), 1.92 (s, 3H), 1.98 (m, 2H), 2.69 (sextet, 1H, J=6 Hz), 3.26 (m, 2H), 3.98 (d, 1H, J=13 Hz), 4.34 (m, 1H), 5.43 (br, 1H), >7.30 (m, 5H). Anal calc. for C$_{14}$H$_{20}$N$_2$O: C, 72.38; H, 8.68; N, 12.06; found: C, 72.52; H, 8.62; N, 11.97. [a]$_D$= +91.4° (c=2.03, CHCl$_3$, 24° C.).

EXAMPLE 2

(2S,4S)-4-t-Butoxycarbonylamino-2-methyl-1-N-benzylpyrrolidine (12)

To 13.13 g (68.64 mmol) of the cis amino alcohol from Example 1, step f in 200 mL of anhydrous THF held at 20° C. under a nitrogen atmosphere and anhydrous conditions was added 18.03 g (68.74 mmol) of triphenylphosphine and 2.27 g (68.65 mmol) of phthalimide. To this solution was added 10.90 mL (69.22 mmol) of diethyl azodicarboxylate (DEAD) dropwise over 15 minutes. The reaction was stirred for 20 minutes and the solvent was removed. The residue was dissolved in 100 mL of ethanol and 3.35 mL (69.06 mmol) of hydrazine monohydrate was added. The mixture was heated at reflux under nitrogen for 3 hours, 15 mL of concentrated hydrochloric acid was added and the yellow precipitate was filtered off and washed with ethanol. The filtrate was concentrated to dryness, the residue dissolved in water and filtered. The filtrate was concentrated, the residue dissolved in 400 mL of water and extracted with ether to remove residual triphenylphosphine The aqueous solution was adjusted to pH 14 with 20% sodium hydroxide solution, extracted with ether, the extracts washed with water and dried over magnesium sulfate and the solvent was removed to give a greenish oil. This oil was dissolved in 150 mL of methanol and 40 mL of water. Di-t-butyldicarbonate (16.50 g, 75.60 mmol) was added in several portions while holding the temperature at 0° C. The temperature was slowly raised to room temperature and the mixture was stirred for 15.5 hours. The solvents were removed, the residue was dissolved in 200 mL of methylene chloride. This was washed with water, dried over magnesium sulfate and concentrated to give a white solid. The solid was purified by chromatography on silica gel, eluting with 100:5:0.5 methylene chloride:methanol:ammonium hydroxide to afford 18.42 g (92.4% yield) of the title product as a white solid. MS M/Z: 291 (M+H). NMR (CDCl$_3$) δ: 1.15 (d, 3H, J=6 Hz), 1.41 (s, 9H), 1.72 (m, 1H), 1.93 (m, 2H), 2.63 (m, 1H), 3.21 (d, 1H, J=13 Hz), 3.26 (m, 1H), 3.98 (d, 1H, J=13 Hz), 4.07 (m, 1H), 4.48 (br, 1H). [a]= +94.5° (c=1.0, CHCl$_3$, 25°, D line).

EXAMPLE 3

(2S,4S)-4-Acetylamino-2-methylpyrrolidine (II)

A 2.93 g (12.61 mmol) sample of (2S,4S)-4-acetylamino-2-methyl-1-N-benzylpyrrolidine, from Example 1, step g above, was dissolved in 50 mL of methanol, 0.60 g of 10% Pd/C was added and the mixture shaken under 4 atm of hydrogen at room temperature for 13 hours. The mixture was concentrated, the catalyst was removed by filtration, and the solvent removed to afford 1.688 g (94.1% yield) of the title compound as a white solid. MS M/Z: 143 (M+H). NMR (CDCl$_3$) δ: 1.16 (d, 3H, J=6 Hz), 1.63 (m, 1H), 1.79 (m, 1H), 1.95 (s, 3H), 2.65 (m, 1H), 3.28 (m, 1H), 3.41 (m, 1H), 4.40 (m, 1H), 5.81 (br, 1H).

EXAMPLE 4

(2S,4S)-4-t-Butoxycarbonylamino-2-methylpyrrolidine (II)

A 4.500 g (15.50 mmol) sample of (2S,4S)-4-t-butoxycarbonylamino-2-methyl-1-N-benzylpyrrolidine, from Example 2 above, was dissolved in 150 mL of methanol, 0.90 g of 10% Pd/C was added and the mixture shaken under 4 atm of hydrogen at room temperature for 13 hours. The mixture was concentrated, the catalyst was removed by filtration, and the solvent removed to afford 3.081 g of the title compound as a white solid. MS M/Z: 201 (M+H). NMR (CDCl$_3$) δ: 1.15 (d, 3H, J=6 Hz), 1.44 (s, (1H), 1.54–1.63 (m, 2H), 1.75 (m, 1H), 2.64 (dd, 1H, J=5, J=12 Hz), 3.26 (m, 1H), 3.38 (dd, 1H, J=7, J=12 Hz), 4.12 (br, 1H), 4.63 (br, 1H). IR (KBr): 1685 cm$^{-1}$.

EXAMPLE 5

(S)-N-Benzyl-5-methylpyrrolidin-3-one

Step 5a. (1S)-N-(1-Phenylethyl)-benzylamine (2)

To 91.25 g (0.753 mol) of S-methylbenzylamine in 400 mL of methanol was added 79.93 g (0.750 mol) of benzaldehyde, and the reaction was stirred for 2 hours at room temperature. To this solution was added in portions over a 1 hour period 21.20 g (0.560 mol) of NaBH$_4$ while maintaining the reaction temperature at 20°-28° C. This mixture was stirred at room temperature for 16 hours, then the solvent was removed by evaporation under reduced pressure. The residue was slurried with water and extracted (3×) with methylene chloride. The solvent was washed with water, dried over MgSO$_4$ and concentrated to give 158.29 g of a colorless liquid. This liquid was distilled under reduced pressure to afford 151.20 g (95%) of the title product as a colorless liquid at 116° to 119° C., 4 mm Hg. MS M/Z: 212 (M+H). NMR (CDCl$_3$) δ: 1.37 (d, 3H, J=7 Hz), 1.61 (Br, 1H), 3.58 (d, 1H, J=9 Hz), 3.69 (d, 1H, J=9 Hz), 3.82 (q, 1H, J=7 Hz), 7.23–7.36 (m, 10H).

Step 5b. (1'S,3S)-3-(Benzyl-(1-phenylethyl)amino)-butanoic acid ethyl ester (4)

To a stirred solution of 20.394 g (96.513 mmol) of (S)-alpha-methyl-N-(phenylmethyl)-benzenemethanamine (from Example 5) in 400 mL of THF, cooled to 0° C., was added, over a 10 minute period, 38.61 g (96.525 mmol) of n-butyllithium, and the reaction was stirred for an additional 15 minutes. To this solution was added 10.00 mL (80.427 mmol) of ethyl crotonate with stirring over a 20 minute period, and the solution was stirred for an additional 20 minutes. The reaction was quenched by addition of an excess of saturated ammonium chloride solution, and the mixture was extracted with ether. The ether extract was washed with saturated brine, dried over MgSO4 and concentrated to give a colorless liquid. The crude product was chromatographed on silica gel, eluting with 1:4 ethyl acetate:hexane, and the solvent was removed to afford 24.10 g (92.1%) of the title product as a colorless oil. MS M/Z: 326 (M+H). NMR (CDCl$_3$) δ: 1.13 (d, 3H, J=7 Hz), 1.16 (t, 3H, J=7 Hz), 1.35 (d, 3H, J=7 Hz), 2.10 (dd, 1H, J=14 Hz, J=6 Hz), 2.36 (dd, 1H, J=14 Hz, J=6 Hz), 3.44 (m, 1H), 3.67 (d, 1H, J=14 Hz), 3.74 (d, 1H, J=14 Hz), 3.88–4.07 (m, 3H), 7.19–7.42 (10H). Anal calc. for C$_{21}$H$_{27}$NO$_2$: C, 77.50; H, 8.36 N, 4.30; found: C, 77.46; H, 8.37; N, 4.28.

Step 5c. (S)-3-Aminobutanoic acid ethyl ester (5)

A 69.10 g (0.212 mol) sample of the compound from step 5b above was dissolved in 250 mL of methanol and 6.9 g of 20% Pd(OH)2/C was added. The mixture was shaken under 4 atm of hydrogen at room temperature for 48 hours. The mixture was filtered and the solvent was removed under vacuum to afford 24.74 g (88.8% yield) of the title as a colorless liquid, which was taken directly to the next step.

Step 5d. (S)-3-(Benzylamino)butanoic acid ethyl ester (6)

A 24.74 g (0.189 mol) sample of the compound from step 5c above was dissolved in 200 mL of methanol and benzylated by a procedure similar to that described in Example 4 above. The product was isolated as described and dried to afford 39.58 g (94.8% yield) of the title product as a colorless liquid, which was taken directly to the next step. (NMR data indicated that approx. 28% of the product was the methyl ester.)

Step 5e. (S)-3-[Benzyl(carboxymethyl)amino]butanoic acid diethyl ester (7)

The 39.58 g (0.179 mol) sample of the compound from step 5d above was dissolved in 200 mL of butanone, 29.70 g (0.215 mol) of K2CO3 and 5.409 g (0.036 mol) of NaI were added and the soution heated to reflux. To the refluxing solution was added 21.00 mL (0.189 mol) of ethyl bromoacetate, the reaction was stirred for 14.5 hours, then cooled, filtered and concentrated. The crude product was heated in a kugelrohr apparatus at 70° C. and 0.3 mm Hg to afford 50.70 g (92.2% yield) of the title product as a residual yellow liquid, which was taken diretly to the next step.

Step 5f. (S)-N-Benzyl-5-methylpyrrolidin-3-one (8)

The 50.70 g (0.165 mol) sample of the compound from step 5e above was dissolved in 400 mL of toluene. The solution was cooled to 0° C. and 21.00 g (0.187 mol) of potassium t-butoxide was added in one portion. The reaction was stirred at 0° C. for 0.5 hours and at room temperature for 1.5 hours, then the solvent was removed. The residue was heated at relux in 600 mL of 1N HCl for 6 hours. The solution was basified to ph 10–11 with 10% NaOH solution, then extracted with ether. The solvent was washed with brine, dried over MgSO4 and concentrated to afford 17.28 g (55.4% yield) of the title product as a pale yellow liquid. [a]$_D$= +208.9° (c=1.92, CHCl$_3$, 26° C.). Other analytical data were the same as those given in Example 1e above.

EXAMPLE 6

(2S,4S)-4-Acetylamino-2-methylpyrrolidine

Step 6a. (1′S, 3S)-3-((1-phenylethyl)amino)-butanoic acid ethyl ester (13)

A 1.30 g (4.01 mmol) sample of (1S, 3S)-3-(benzyl-(1-phenylethyl)-amino)-butanoic acid ethyl ester, from Example 5b above, was dissolved in 15 mL of methanol to which was added 0.20 g of 10% Pd/C and 0.65 mL of conc. HCl. The mixture was stirred under a hydrogen atmosphere for 1 hour at room temperature, then filtered, and the filtrate concentrated to afford 1.04 g (95.9% yield) of a white HCl salt. This salt was dissolved in water, adjusted to pH 12 with 10% NaOH and extracted with ether. The solvent was washed with saturated brine, dried over $MgSO_4$ and concentrated to afford 0.90 g (95.5% yield) of the title product as a colorless liquid. MS M/Z: 236 (M+H). NMR ($CDCl_3$) δ: 1.05 (d, 3H, J=7 Hz), 1.26 (t, 3H, J=7 Hz), 1.32 (d, 3H, J=7 Hz), 1.55 (br, 1H), 2.36 (dd, 1H, J=14 Hz, J=6 Hz), 2.43 (dd, 1H, J=14 Hz, J=6 Hz), 2.98 (sextet, 1H, J=7 Hz), 3.88 (q, 1H, J=7 Hz), 4.13 (q, 2H, J=7 Hz), 7.22-7.32 (m, 5H).

Step 6b. (1′S,3S)-3-((1-phenylethyl)(carboxymethyl)amino)butanoic acid diethyl ester (14)

A 2.00 g (18.50 mmol) sample of the compound from Example 6a above, 2.40 g of $K_2CO_3$ and 1.27 g of NaI were dissolved in butanone, then the reaction was heated to reflux under $N_2$. Ethyl bromoacetate (1430 μL) was added dropwise, and the reaction continued at reflux for 22 hours. The solution was filtered and concentrated, and the residue subjected to treatment in a kugelrohr apparatus, the chromatographed over silica gel, eluting with 1:4 ethyl acetate:hexane. Removal of the solvent afforded 2.474 g (90.6% yield) of the title product as a colorless liquid. MS M/Z: 322 (M+H). NMR ($CDCl_3$) δ: 1.06 (d, 3H, J=7 Hz), 1.21 (t, 3H, J=7 Hz), 1.23 (t, 3H, J=7 Hz), 1.36 (d, 3H, J=7 Hz), 2.15 (dd, 1H, J=12 Hz, J=8 Hz), 2.55 (dd, 1H, J=12 Hz, J=6 Hz), 3.30 (d, 1H, J=17 Hz), 3.37 (d, 1H, J=17 Hz), 3.49 (m, 1H), 4.09 (m, 4H), 7.20-7.39 (m, 5H).

Step 6c. (1′S,5S)-N-(1-phenylethyl)-5-methyl-3-pyrrolidinone (15)

Following the procedures of Example 5f, a 2.47 g sample of the compound from step 6b above was reacted, and 1.37 g (87.6% yield) of the title product was isolated as a pale yellow liquid after an additional chromatography step (silica gel, eluting with 1:4 ethyl acetate:hexane). This compound is unstable and was taken directly to the next step. MS M/Z: 204 (M+H). NMR ($CDCl_3$) δ: 1.15 (d, 3H, J=7 Hz), 1.38 (d, 3H, J=7 Hz), 2.12 (dd, 1H, J=18 Hz, J=6 Hz), 2.60 (dd, 1H, J=18 Hz, J=7 Hz), 2.85 (d, 1H, J=18 Hz), 2.91 (d, 1H, J=18 Hz), 3.55 (sextet, 1H, J=7 Hz), 3.94 (q, 1H, J=7 Hz), 7.23-7.38 (m, 5H).

Step 6d. (1′S,2S)-4-Hydroxy-1-(1-phenylethyl)-2-methylpyrrolidine

A 2.602 g sample of the compound from step 6c was dissolved in 30 mL of methanol and cooled to −78° C. Then 0.581 g of $NaBH_4$ was added and stirred for 2 hours at −78° C. then at room temperature for 16 hours. The mixture was concentrated to dryness, the residue slurried with water and 20% NaOH and extracted with ether. The solvent was extracted with brine, dried over $MgSO_4$ and concentrated to afford 2.563 g (97.6% yield) of the title product as a pale yellow oil. The NMR spectrum indicated an 8:1 mixture of the cis/trans isomers. The isomers were not separated, but the mixture was carried forward to the next step.

Step 6e. (1′S,2S)-4-Amino-1-(1-phenylethyl)-2-methylpyrrolidine

A 2.563 g (12.485 mmol) sample of the compound from step 6d above was dissolved in 30 mL of THF, and 3.307 g (12.61 mmol) of triphenyl phosphine and 1.855 g (12.61 mmol) of phthalimide was added. To the stirred suspension at 20° C. was added 2.50 mL (12.70 mmol) of DIPAD dropwise, and the mixture was stirred for 30 minutes. The solution was concentrated to dryness, the residue was dissolved in 20 mL of anhydrous ethanol and 0.61 mL (12.58 mmol) of hydrazine hydrate was added, and the mixture was heated at reflux under $N_2$ for 2.5 hours. four mL of conc. HCl were added and the mixture was filtered. The filtrate was concentrated, the residue was dissolved in water, and the solution was extracted with methylene chloride. The aqueous solution was basified to pH 14 and extracted with methylene chloride. The solvent was washed with water, dried over $MgSO_4$ and concentrated to give a brownish liquid. This liquid was subjected to distillation in a kugelrohr apparatus at 0.2 mm Hg and 100°-120° C. to afford 2.20 g (86.2% yield) of the title product as a colorless liquid, which was taken directly to the next step.

Step 6f. (1S,5S)-4-Acetylamino-1-(1-phenylethyl)-2-methylpyrrolidine

A 2.20 g (10.77 mmol) sample of the compound from step 6e above was dissolved in 5 mL of methylene chloride and cooled to 0° C. Triethylamine (1.65 mL, 11.84 mmol) and acetic anhydride (1.10 mL, 11.66 mmol) were added and the mixture was stirred for 2 hours at room temperature. The solution was diluted, washed with water, dried over $MgSO_4$ and concentrated to give a yellow oil, which solidified upon standing. This material was chromatographed on silica gel, eluting with 100:5:0.5 methylene chloride:methanol:ammonia, removing the solvent and drying to afford 1.927 g (72.6% yield) of the title product as a solid (exclusively trans isomer). MS M/Z:247 (M+H). NMR ($CDCl_3$) δ: 0.96 (d, 3H, J=7 Hz), 1.31 (m, 1H), 1.36 (d, 3H, J=7 Hz), 1.91 (s, 3H), 1.95 (m, 1H), 2.23 (dd, 1H, J=10 Hz, J=6 Hz), 2.94 (dd, 1H, J=10 Hz, J=8 Hz), 3.27 (m, 1H), 3.69 (q, 1H, J=7 Hz), 4.38 (m, 1H), 5.58 (br, 1H), 7.23-7.35 (m, 5H).

Step 6g. (2S,4S)-4-Acetylamino-2-methylpyrrolidine (II)

Removal of the alpha-methylbenzyl group via hydrogenolysis is accomplished by a procedure similar to that of Example 3 to give the title pyrrolidine.

EXAMPLE 7

(2S,4S)-1-BOC-4-Acetylamino-2-methylpyrrolidine

Step 7a. (D)-N-Benzyloxycarbonylaspartic acid (22)

A 50 g (0.375 mol) sample of D-aspartic acid was dissolved in a mixture of DMF and diisopropylethylamine, and 114 g (0.45 mol) of N-(benzylcarbonyloxy)-succinamide was added and the reaction was stirred at 70° C. for 2 hours. The solvent was removed under vacuum, and the residue dissolved in methylene chloride which was extracted with pH 2 HCl, water, and brine and dried over $MgSO_4$. The solvent was removed and the residual oil triturated with ether and methanol; the title product (92.75 g; 92.5% yield) separated upon cooling.

Step 7b. (R)-N-Benzyloxycarbonylaspartic anhydride (23)

A 92.75 g sample of the compound from step 7a above was dissolved in acetic anhydride and stirred at room temperature overnight. The solvent was removed under vacuum at a temperature less than 38° C. to afford the title product in a quantitative yield.

Step 7c. (R)-4-Benzyloxycarbonylamino-2-oxo-tetrahydrofuran (24)

A 42.0 g (0.168 mol) sample of the compound from step 7b above was dissolved in THF and added over a 2 hour period to a slurry of 6.35 g (0.168 mol) of $NaBH_4$ in THF held at 0° C. The reaction was stirred for an additional 2 hours and adjusted to pH 2 with 6N HCl. The mixture was taken to dryness, and the residue was dissolved in water and extracted with ether. The solvent was washed with salturated brine, dried over $MgSO_4$ and concentrated in a vacuum. The residue was stirred in 50 mL of acetic anhydride for two hours. The excess solvent was removed by distillation in a kugelrohr apparatus, and the residue was triturated with ether to afford 20.5 g (63.7% yield) of the title product as a white solid. MS M/Z: 203 (M+H). NMR ($CDCl_3$) δ: 2.46 (dd, 1H, J=18 Hz, J=4 Hz), 2.84 (dd, 1H, J=18 Hz, J=8 Hz), 4.22 (m, 1H), 4.49 (m, 2H), 5.11 (s, 2H), 5.27 (br, 1H), 7.34 (m, 5H).

Step 7d. (R)-4-Amino-2-oxo-tetrahydrofuran hydrobromide (25)

A 10.0 g sample of the compound from step 7c above was dissolved in acetic acid containing 5 equiv. of 30% HBr, then 10 mL of ether was added and the mixture was stirred for 2 hours at room temperature. Upon cooling the title compound (6.15 g, 86.6% yield) precipitated as white crystals. NMR ($CDCl_3$) δ: 2.50, (dd, 1H, J=18 Hz, J=3 Hz), 3.12 (dd, 1H, J=18 Hz, J=9 Hz), 4.13 (m, 1H), 4.28 (dd, 1H, J=12 Hz, J=3 Hz), 4.51 (dd, 1H, J=12 Hz, J=7 Hz), 8.20 (br, 3H).

Step 7e. (R)-4-Benzylamino-2-oxo-tetrahydrofuran (26)

A 6.15 g (0.037 mol) sample of the compound from step 7d above was dissolved in methanol along with 5.16 mL (0.037 mol) of triethylamine. To this was added 3.76 mL (0.037 mol) of benzaldehyde, and the reaction was stirred for 1 hour at room temperature. To this was added 2.79 g (0.074 mol) of $NaBH_4$ in portions, and the reaction was stirred for 0.5 hour. The solvent was remove, and the residue was slurried with water and extracted with methylene chloride. Removal of the solvent gave a yellow oil, which was chromatographed on silica gel, eluting with 100:10:0.5 methylene chloride:methanol:ammonia to afford after drying 5.0 g (70.6% yield) of the title compound as a yellow oil. MS M/Z: 192 (M+H), 209 (M+$NH_4$). NMR ($CDCl_3$) δ: 2.37 (dd, 1H, J=18 Hz, J=4 Hz), 1.63 (br, 1H), 2.68 (dd, 1H, J=18 Hz, J=7 Hz), 3.67 (m, 1H), 3.75 (d, 1H, J=13 Hz), 3.81 (d, 1H, J=13 Hz), 4.10 (dd, 1H, J=13 Hz, J=4 Hz), 4.35 (dd, 1H, J=13 Hz, J=6 Hz), 7.30 (m, 5H).

Step 7f. (R)-4-[Benzyl(ethoxycarbonylmethyl)amino]-2-oxo-tetrahydrofuran (27)

A 5.0 g (26 mmol) sample of the compound from step 7e above, 5.76 mL (52 mmol) of ethyl bromoacetate and 4.0 mL (28 mmol) of triethylamine dissolved in toluene was heated at reflux for 2 hours. The solvent was removed and the residue was slurried with water and extracted with methylene chloride. The solution was dried over $MgSO_4$, and the solvent removed. The residue was chromatographed on silica gel, eluting with 10% methanol, to afford after drying 5.8 g (80.3% yield) of the title product as a yellow liquid. MS M/Z: 278 (M+H). NMR ($CDCl_3$) δ: 1.26 (t, 3H, J=7 Hz), 2.60 (dd, 1H, J=18 Hz, J=8 Hz), 2.69 (dd, 1H, J=18 Hz, J=8 Hz), 3.77 (d, 1H, J=14 Hz), 3.86 (d, 1H, J=14 Hz), 4.01 (app. pentet, 1H, J=7 Hz), 4.14 (q, 2H, J=7 Hz), 4.22 (dd, 1H, J=10 Hz, J=7 Hz), 4.43 (dd, 1H, J=10 Hz, J=7 Hz), 7.31 (m, 5H).

Steps 7g. (R)-1-Benzyl-5-hydroxymethyl-3-pyrrolidinone (29)

A 0.890 g (3.2 mmol) sample of the compound from step 7f above was dissolved in THF, and the solution was cooled to 0° C. To this solution was added 3.52 mL (3.52 mmol) of a 1N solution of sodium bis(trimethylsilyl)amide and the solution was stirred under $N_2$ at 0° C. for 20 minutes. The solvent was removed under vacuum, and the residue was dissolved in 1N HCl and heated at reflux for 0.5 hours. The solution was made basic with $Na_2CO_3$ and extracted with methylene chloride. The extract was washed with brine, dried over $MgSO_4$ and conventrated to leave a dark residue. The crude product was chromatographed on silica gel, eluting with ethyl acetate, to afford after drying 253 mg (38.6% yield) of the title product as an unstable brown oil. MS M/Z: 206 (M+H). NMR ($CDCl_3$) δ: 2.38 (br, 1H), 2.44 (dd, 1H, J=19 Hz, J=8 Hz), 2.62 (dd, 1H, J=19 Hz, J=7 Hz), 2.82 (d, 1H, J=18 Hz), 3.18 (m, 1H), 3.35 (d, 1H, J=18 Hz), 3.41 (d, 1H, J=14 Hz), 3.58 (dd, 1H, J=12 Hz, J=2 Hz), 3.96 (dd, 1H, J=12 Hz, J=3 Hz), 4.18 (d, 1H, J=14 Hz), 7.31 (m, 5H).

Step 7h. (R)-1-BOC-5-hydroxymethyl-3-pyrrolidinone (30)

A mixture of the compound from step 7g above, di-t-butyl carbonate, and 10% Pd/C in methanol is stirred under $H_2$, and the title product is isolated by filtration and removal of the solvent.

Step 7i. (R)-1-BOC-5-methanesulfonyloxymethyl-3-pyrrolidinone (31)

To a solution of the compound from step 7h above in methylene chloride is added triethylamine and methansulfonyl chloride and stirred at 0° C. When the reaction is complete, the solution is diluted with additional solvent, the solvent is extracted with water, and the solvent dried and removed to yield the title product.

Step 7j. (2S,4R)-1-BOC-4-hydroxy-2-methylpyrrolidine (32)

To a sample of the compound from step 7i above, dissolved in THF and cooled to −30° C., is added lithium triethylborohydride, and the mixture is stirred for two hours. The reaction is quenched, and the product extracted into an organic solvent, which is dried and purified via column chromatography to afford the title product.

Step 7k. (2S,4S)-1-BOC-4-Acetylamino-2-methylpyrrolidine

A sample of the compound from step 7j above is converted into the title product by procedures similar to those given in Example 1g, above.

EXAMPLE 8

Alternate preparation of (2S,4R)-1-BOC-4-Hydroxy-2-methylpyrrolidine

Step 8a. (2S,4R)-4-Hydroxy-2-methylpirrolidine

To a 0.995 g (5.20 mmol) sample of the cis isomer of (2S,4R)-N-benzyl-2-methylpyrrolidin-4-ol, from Example 1f, dissolved in 50 mL of methanol was added 0.1 g of Pd/C, and the mixture was shaken under 4 atm of $H_2$ at room temperature for 24 hours. The mixture was filtered and the solvent removed. The product was taken directly to the next step.

Step 8b. (2S,4R)-1-BOC-4-hydroxy-2-methylpyrrolidin-4-ol (32)

To the sample from step 8a dissolved in 15 mL of methanol was added 1.13 g of di-t-butyl carbonate and 3 mL of water, and the reaction was stirred at room temperature for 5 hours. The solution was taken to dryness under vacuum, and the residue was dissolved in methylene chloride. The solvent was washed with water, dried over MgSO$_4$ and concentrated to dryness. The residue was recrystallized from ethyl acetate/hexane to afford 0.789 g (75.4% yield) of the title product as colorless crystals. The NMR data and TLC behavior are the same as those described for the same compound in U.S. Pat. No. 4,962,112.

EXAMPLE 9

Alternate preparation of (2S,4S)-1-BOC-4-Amino-2-methylpyrrolidine

Step 9a. (2S,4S)-1-BOC-4-benzylamino-2-methylpyrrolidine (34)

To a 90 g (0.322 mol) sample of (2S,4R)-1BOC-4-methanesulfonyloxy-2-methylpyrrolidine, prepared as described in U.S. Pat. No. 4,962,112, was added 345 g (3.22 mol) of benzylamine, and the solution was heated at 100° C. under N$_2$ for 8 hours. The solution was cooled to room temperature and the excess benzylamine removed under vacuum. The residue was dissolved in ethyl acetate and washed with water. The product was then extracted into 1.0M citric acid, which was then adjusted to pH 11.5 with conc. ammonium hydroxide solution. The product was extracted into ethyl acetate, which was dried over Na$_2$SO$_4$, filtered, and concentrated. After drying, 76.2 g (81.5% yield) of the title product was obtained as a yellow oil.

Step 9b. (2S,4S)-1-BOC-4-amino-2-methylpyrrolidine (35)

To a 1.95 g (6.71 mmol) sample of the compound from step 9a dissolved in 40 mL of absolute ethanol, stirred under nitrogen, was added 0.5 g of 10% Pd/C and 2.06 g (32.7 mmol) of ammonium formate. The temperature was raised to 60° C., and the reaction was stirred for 1 hour. The catalyst was filtered off, and the filtrate was concentrated under vacuum to afford after drying 1.38 g (100% yield) of the title compound as a viscous oil.

Step 9c. (2S,4S)-1-BOC-4-acetylamino-2-methylpyrrolidine (36)

A 46 g (0.230 mol) sample of the compound from step 9b above was dissolved in 335 mL of pyridine. To this solution stirred under N$_2$ was added 46.5 g (0.459 mol) of triethylamine, and the solution was cooled to −5° C. using an ice/methanol bath. To this was added dropwise 46.9 g (0.459 mol) of acetic anhydride while maintaining the temperature at 0° C. After the addition was complete, the solution was allowed to warm to room temperature with stirring for 2 hours. The solvent was removed under vacuum to leave an oil, which was dissolved in chloroform and washed with a 7% HCl solution, saturated NaHCO$_3$ solution, and saturated brine, then dried over Na$_2$SO$_4$. The solvent was removed to leave a pale yellow oil, which was triturated with hot hexane and cooled to allow crystallization. The 50.6 g (90.9% yield) of crude product was isolated by filtration and chromatographed on silica gel, eluting with 20% hexane in ethyl acetate to afford 40.9 g of products. A final crystallization from ether gave the pure title product (31.6 g, 56.8% yield).

EXAMPLE 10

(2S,4R)-4-Acetylamino-2-methylpyrrolidine

Step 10a. (2S,4R)-4-Acetylamino-1-benzyl-2-methylpyrrolidine

The trans product (2S,4S)-N-benzyl-2-methylpyrrolidinol, the minor product isolated in Example 1f above, was reacted via procedures as described in Example 1g to afford the title product as a white crystalline solid after recrystallization from ethyl acetate/hexane 1/5. MS M/Z: 233 (M+H). NMR (CDCl$_3$) δ:1.22 (d, 3H, J=6 Hz), 1.30 (m, 1H), 1.90 (s, 3H), 2.42 (m, 3H), 2.71 (d, 1H, J=10 Hz), 3.13 (d, 1H, J=13 Hz), 4.03 (d, 1H, J=13 Hz), 4.32 (m, 1H), 5.90 (br, 1H), 7.29 (m, 5H).

Step 10b. (2S,4R)-4-Acetylamino-2-methylpyrrolidine

The product from step 10a is deprotected via hydrogenolysis by a procedure similar to that of Example 3 above to afford the title compound.

EXAMPLE 11

(2S,4S)-4-5-Butoxycarbonylamino-2-methylpyrrolidine

Step 11a. (2S,4S)-4-5-Butoxycarbonylamino-1-benzyl-2-methylpyrrolidine

The trans product (2S,4S)-N-benzyl-2-methylpyrrolidinol, the minor product isolated in Example 1f above, was reacted via the procedures described in Example 2 to afford the title product as a colorless oil. MS M/Z: 291 (M+H). NMR (CDCl$_3$) δ:1.19 (d, 1H, J=6 Hz), 1.29 (m, 1H), 1.41 (s, 9H), 2.39 (m, 3H), 2.71 (d, 1H, J=10 Hz), 3.10 (d, 1H, J=13 Hz), 4.01 (d, 1H, J=13 Hz), 4.03 (m, 1H), 4.86 (br, 1H), 7.29 (m, 5H).

Step 11b. (2S,4S)-4-5-Butoxycarbonylamino-2-methylpyrrolidine

The product from step 11a was deprotected via hydrogenolysis via a procedure similar to that of Example 4 above to afford the title compound as a white solid. MS M/Z: 201 (M+H). NMR (CDCl$_3$) δ:1.25 (d, 3H, J=6 Hz), 1.44 (s, 9H), 2.39 (m, 1H), 2.93 (dd, 1H, J=11, J=4 Hz), 3.13 (m, 3H), 4.14 (br, 2), 5.06 (br, 1H).

EXAMPLE 12

(+,−)-trans-4-Acetylamino-1-benzyl-2-methylpyrrolidine

By reacting (+,−)-N-benzyl-5-methylpyrrolidin-3-one (prepared according to Prost et al., Helv. Chim Acta, 52:1134 (1969)) according to the procedures described in Examples 1f and 1g above, the title compound was obtained as a crystalline solid. MS M/Z: 233 (M+H). NMR (CDCl$_3$) δ: 1.15 (d, 3H, J=6 Hz), 1.73 (m, 1H), 1.91 (s, 3H), 1.98 (m, 1H), 2.7–0 (sextet, 1H, J=6 Hz), 3.27 (m, 2H), 3.98 (d, 1H, J=13 Hz), 4.34 (m, 1H), 5.45 (br, 1H), 7.29 (m, 5H).

We claim:

1. A compound having the formula

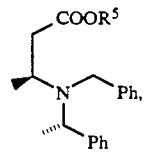

wherein Ph is phenyl and R$^5$ is selected from the group consisting of hydrogen and loweralkyl.

2. A compound having the formula

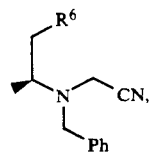

wherein Ph is phenyl and R⁶ is selected from the group consisting of hydroxy, halo and cyano.

3. A compound having the formula

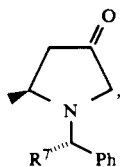

wherein Ph is phenyl and R⁷ is selected from the group consisting of hydrogen and methyl.

4. A compound having the formula

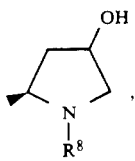

wherein R⁸ is selected from the group consisting of —CH₂C₆H₅ and —CH(CH₃)C₆H₅.

5. A compound according to claim 4, wherein the chiral carbon atom at C-4 has the R configuration.

6. A compound according to claim 4, wherein the chiral carbon atom at C-4 has the S configuration.

7. A compound having the formula

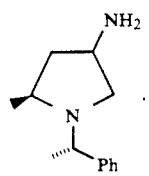

8. A compound having the formula

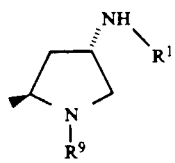

wherein R¹ is selected from the group consisting of t-BOC and acetyl, and R⁹ is selected from the group consisting of —CH₂C₆H₅ and —CH(CH₃)C₆H₅.

9. A compound according to claim 8, wherein the chiral carbon atom at C-4 has the R configuration.

10. A compound according to claim 8, wherein the chiral carbon atom at C-4 has the S configuration.

11. A process for the preparation of a trans-configuration amino-protected 4-amino-2-methylpyrrolidine compound having the formula

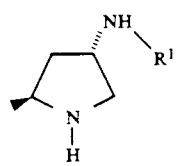

comprising the step of selectively crystallizing a corresponding trans-configuration N-1-protected intermediate of the formula

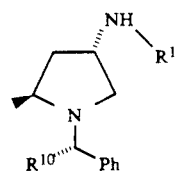

from a (4R)- and (4S)-configuration mixture of said intermediate, wherein R¹ is selected from the group consisting of t-BOC and acetyl, and R¹⁰ is selected from the group consisting of hydrogen and methyl.

* * * * *